United States Patent
Duetsch et al.

(10) Patent No.: US 6,287,578 B1
(45) Date of Patent: Sep. 11, 2001

(54) CONDENSATION PRODUCTS CONTAINING POLYETHER-MODIFIED MONOESTERS AND/OR -AMIDES OF α, β-UNSATURATED DICARBOXYLIC ACIDS, THEIR PREPARATION AND USE

(75) Inventors: Michael Duetsch; Burghard Gruning; Jorg Simpelkamp; Christian Weitemeyer, all of Essen (DE)

(73) Assignee: Th. Goldschmidt AG, Essen (DE)

( * ) Notice: Subject to any disclaimer, the term of this patent is extended or adjusted under 35 U.S.C. 154(b) by 0 days.

(21) Appl. No.: 09/312,221

(22) Filed: May 14, 1999

(30) Foreign Application Priority Data

May 20, 1998 (DE) ............................................. 198 22 604

(51) Int. Cl.$^7$ ...................................................... A61K 6/00
(52) U.S. Cl. ............................................................ 424/401
(58) Field of Search ..................... 424/400, 401; 562/595, 234; 568/780, 585, 709, 375, 446; 526/59; 560/179, 126, 55; 528/363

(56) References Cited

U.S. PATENT DOCUMENTS

| 4,137,245 | * | 1/1979 | Christiansen ..................... 260/404.5 |
| 5,219,952 |  | 6/1993 | Koskan et al. . |
| 5,521,279 | * | 5/1996 | Wood et al. .......................... 528/363 |
| 5,880,299 | * | 3/1999 | Ponsati Obiols et al. ............ 554/109 |
| 5,912,284 | * | 6/1999 | Hirata et al. ............................. 524/5 |

FOREIGN PATENT DOCUMENTS

| 36 26 672 A1 | 2/1988 | (DE) . |
| 43 00 020 A1 | 7/1994 | (DE) . |
| 43 27 494 A1 | 2/1995 | (DE) . |
| 44 20 642 A1 | 12/1995 | (DE) . |
| 195 25 365 A1 | 1/1997 | (DE) . |
| 195 45 678 A1 | 6/1997 | (DE) . |
| 0 578 449 A1 | 1/1994 | (EP) . |
| 0 578 450 A3 | 1/1994 | (EP) . |
| 0 612 784 A1 | 8/1994 | (EP) . |
| 0 659 875 A2 | 6/1995 | (EP) . |
| WO 92/14753 | 9/1992 | (WO) . |
| WO 95/35337 | 12/1995 | (WO) . |

OTHER PUBLICATIONS

Kovaks, et al., "Synthesis and Inhibitory Activity of Polyaspartic Acid Derivatives," J. Med. Chem., vol. 10, pp. 904–907 (1967).

Neuse, et al., "Water–Soluble Polyamides as Potential Drug Carriers," Applied Macromolecular Chemistry and Physics, vol. 192, pp. 35–50 (1991).

Cammas, et al., "Functional Poly [(Ethylene Oxide)–Co–(β–Benzyl–L–Aspartate)] Polymeric Micelles: Block Copolymer Synthesis and Micelles Formation," Macromol. Chem. Phys., vol. 196, pp. 1899–1905 (1995).

* cited by examiner

Primary Examiner—Dameron L. Jones
(74) Attorney, Agent, or Firm—Scully, Scott, Murphy & Presser

(57) ABSTRACT

The present invention describes condensation products of polyether-modified and optionally hydrophobically modified monoesters and/or -amides of α, β-unsaturated dicarboxylic acids and ammonia, their preparation and use.

The condensation products contain polyoxyalkylene chains bonded via ester and/or amide bonds and prepared from monoesters and/or monoamides of monoethylenically unsaturated dicarboxylic acids and ammonia or prepared from the ammonium salts of said acids, and the mixtures thereof, optionally in the presence of cocondensable compounds.

15 Claims, No Drawings

CONDENSATION PRODUCTS CONTAINING POLYETHER-MODIFIED MONOESTERS AND/OR -AMIDES OF α, β-UNSATURATED DICARBOXYLIC ACIDS, THEIR PREPARATION AND USE

BACKGROUND OF THE INVENTION

1. Technical Field

The present invention describes condensation products of polyether-modified and optionally hydrophobically modified monoesters and/or -amides of α,β-unsaturated dicarboxylic acids and ammonia, their preparation and use.

2. Prior Art

Polyamino acid derivatives, in particular polyaspartic acid, have recently attracted particular attention because of their properties, in particular their biodegradability and their similarity to naturally occurring structures. Proposed applications are inter alia as biodegradable complexing agents, water softeners and detergent builders. Polyaspartic acid is generally obtained by alkaline hydrolysis of the direct synthesis precursor polysuccinimide (PSI, anhydropolyaspartic acid), the cyclic imide of polyaspartic acid. PSI can be prepared, for example, in accordance with EP 0 578 449 A, WO 92/14753, EP 0 659 875 A or DE 44 20 642 A from aspartic acid, or is obtainable, for example according to DE 36 26 672 A, EP 0 612 784 A, DE 43 00 020 A or U.S. Pat. No. 5, 219, 952 A, from maleic acid derivatives and ammonia. Proposed applications for these customary polyaspartic acids are inter alia as encrustation inhibitors, builders in detergents, fertilizer additive and auxiliary in tanning.

DE 4327494, EP 0578449 and EP 0578450 describe the preparation of polysuccinimide from aspartic acid or maleic acid derivatives in polyethylene glycols as solvents. Here, there is no incorporation of the polyether into the product.

The reaction of polysuccinimide with amines, which has been described by various working groups, leads to polyaspartic amides (Kovacs et al., J. Med. Chem. 1967, 10, 904–7; Neuse, Angew. Makromol. Chem. 1991, 192, 35–50). The ring opening of polysuccinimide using polyamines and the subsequent alkaline hydrolysis for the preparation of polyaspartic acid derivatives for applications as superabsorbers is described, for example, in WO 95/35337. DE 19525365 describes the modification of polysuccinimide with amines and amino-functional polyethers for the preparation of paper auxiliaries.

Kataoka et al. describe, in Macromol. Chem. Phys. 1995, 196, 1899–1905, poly-L-aspartic benzyl ester with terminally linked polyether block for pharmaceutical uses. The preparation of these enantiomerically pure products, however, proceeds via the N-carboxy anhydrides of L-aspartic acid and is very complex and uneconomical.

For applications inter alia as emulsifier, dispersant and surfactant, copolymeric polyaspartic esters partially esterified with long-chain fatty alcohols or their derivatives are of particular interest. Such compounds are readily obtainable on the basis of maleic monoesters and ammonia, as explained in DE 195 45 678 A or EP 96 118 806.7 A.

A disadvantage in the property profile of such polyaspartic acid derivatives having carboxylate side chains as hydrophilic component is, however, the pH dependency of the behavior. Changes in the pH cause undesired changes in the hydrophilicity, e.g. as a result of protonation of carboxylate groups, which is noticeably a disadvantage in their application properties, e.g. as regards the pH, thermal and long-term stability of the preparations, for example in the field of cosmetic W/O and O/W emulsions.

The object of the present invention is therefore to provide copolymeric polyaspartic acid derivatives having improved application properties which also contain nonionic hydrophilic groups.

SUMMARY OF THE INVENTION

The object is achieved according to the present invention by condensation products of polyether-modified and optionally of hydrophobically modified monoesters and/or -amides of α,β-unsaturated dicarboxylic acids and ammonia.

DETAILED DESCRIPTION OF THE INVENTION

The novel condensation products can be obtained by a preparation process which involves reacting a mixture of monoesters and/or monoamines of monoethylenically unsaturated dicarboxylic acids with ammonia, or thermally converting the ammonium salts of these acids into the polymer. Use can be made, for example, of ester and amide derivatives of maleic acid, fumaric acid, itaconic acid, alkenylsuccinic acid, alkylmaleic acid, citraconic acid or their ammonium salts, preferably derivatives of maleic acid, fumaric acid or itaconic acid, particularly preferably maleic acid derivatives of the general formulae (I) and (II)

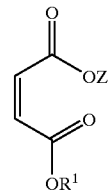

(I)

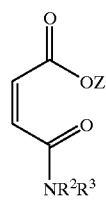

(II)

where $R^1$ can be as defined for $R^4$, $R^5$ and $R^6$, $R^2$ is indentical or different, straight-chain or branched, saturated or unsaturated alkyl, alkenyl or aryl radicals having from 1 to 30 carbon atoms, is hydroxy- or aminoalkyl having from 2 to 30 carbon atoms, each optionally oxa- or aza-substituted, having from 1 to 6 hydroxyl groups and/or from 1 to 6 amino groups, is their acylation products with $C_1$ to $C_{22}$ carboxylic acid radicals, or is polyoxyalkylene radicals of the type $R^{12}X(C_nH_{2n-m}R^{13}{}_mO)_oR^{14}$, where X is oxygen or NH, $R^{12}$ is identical or different divalent alkyl, alkenyl or aryl radicals having from 2 to 30 carbon atoms, $R^{13}$ is hydrogen and/or identical or different alkyl, alkenyl or aryl radicals having from 1 to 30 carbon atoms, $R^{14}$ is hydrogen, identical or different alkyl, alkenyl, aryl or acyl radicals having from 1 to 30 carbon atoms, n is 2 or 4, m assumes values from 0 to 4 and o assumes values from 1 to 100, or assumes the meaning of $R^5$, and $R^3$ is hydrogen or a radical $R^2$, $R^4$ is identical or different, straight-chain or branched, saturated or unsaturated hydroxy-functional alkyl or alkenyl radicals having from 1 to 30 carbon atoms and from 1 to 20 hydroxyl groups or their acylation products with 1 to 22 carboxylic acid radicals, or is polyoxyalkylene radicals of the type $R^{12}X(C_nH_{2n-m}R^{13}{}_mO)_oR^{14}$, where X is oxygen or the radical —NH—, $R^{12}$ is identical or different divalent alkyl, alkenyl or aryl radicals having from 2 to 30 carbon atoms, $R^{13}$ is hydrogen and/or identical or different alkyl, alkenyl or aryl radicals having from 1 to 30 carbon atoms, $R^{14}$ is hydrogen, identical or different alkyl, alkenyl or aryl radicals having from 1 to 30 carbon atoms, n is 2 or 4, m assumes values from 0 to 4 and o assumes values from 1 to 100, $R^5$ is identical or different, straight-chain or branched, saturated or unsaturated alkyl or alkenyl radicals $R^7$ having from 6 to 30 carbon atoms or is radicals of the structure —Y—$R^7$, where Y assumes the meaning of polyoxyalkylene radicals of the type $(C_nH_{2n-m}R^{13}{}_mO)_o$, where $R^{13}$ is hydrogen and/or identical or different alkyl, alkenyl or aryl radicals having from 1 to 30 carbon atoms, n is 2 or 4, m assumes values from 0 to 4, and o assumes values from 1 to 100, and $R^6$ is identical or different, straight-chain or branched, saturated or unsaturated alkyl or alkenyl radicals having from 1 to 5 carbon atoms, Z is one or more radicals from the group of alkali metals, alkaline earth metals, hydrogen or ammonium, $[NR^8R^9R^{10}R^{11}]^+$, where $R^8$ to $R^{11}$ are in each case independently of one another hydrogen, identical or different, straight-chain or branched, saturated or unsaturated alkyl radicals, alkenyl radicals or hydroxyfunctional alkyl radicals having from 1 to 22 carbon atoms and optionally from 1 to 6 hydroxyl groups, and at least one radical $R^2$, $R^3$ or $R^4$ contains a polyoxyalkylene chain having from 2 to 100 units, which in the case of $R^4$ is not like said radicals Y bonded to a radical $R^7$.

As usual, all of the data given relating to the composition of the polymeric products refer to the average composition of the polymer chains.

Use is made of mixtures having a total content of from 1 to 100% by weight, preferably from 40 to 100% by weight, of ester components (I) and having a content of from 0 to 99% by weight, preferably from 0 to 60% by weight, of amide components (II). The proportion by weight of the polyoxyalkylene chains in the reaction mixture is from 1 to 95% by weight, preferably from 20 to 80% by weight. The reaction requires the use of from 0.5 to 5 equivalents of ammonia, preferably from 0.8 to 2 equivalents, in gaseous form or in solution.

Maleic acid derivatives of type (I) in which $R^1$ assumes the meaning of $R^4$ and which are used according to the invention can be esters of hydroxyl-terminal alkylene oxide polymers, e.g. those based on ethylene oxide, propylene oxide, butylene oxide, styrene oxide and/or long-chain olefin oxides or tetrahydrofuran, preferably esters of polyethylene glycol and ethylene oxide-propylene oxide copolymers. Other preferred maleic esters of this type are derived from polyalkylene glycols having a hydroxyl function on a terminus and an alkyl or acyl function on the other chain end, particularly preferably addition products of from 2 to 100 mol of ethylene oxide and/or propylene oxide with mono- or polyfunctional alcohols, amines, aminoalcohols or carboxylic acids having from 1 to 5 carbon atoms, such as, for example, methanol, ethanol, the isomeric propanols and butanols, allyl alcohol, ethylene glycol, ethanolamine, propylene glycol, glycerol, acetic acid and monoacylation products of polyalkylene glycols, for example with carboxylic acids having from 1 to 4 carbon atoms.

Preferred radicals $R^5$ are alkyl radicals having from 8 to 30 carbon atoms, for example linear or branched decyl, dodecyl, tetradecyl, hexadecyl, or octadecyl radicals and unsaturated alkenyl radicals, such as, for example, oleyl.

Preferred radicals $R^6$ are alkyl radicals having from 1 to 4 carbon atoms, preferably methyl, ethyl, n-propyl, i-propyl, n-butyl, i-butyl, s-butyl.

The units (II) are preferably derived from primary or secondary amines $NR^2R^3H$, in which $R^2$ is as defined above, for example branched or linear octyl, decyl, dodecyl, tetradecyl, hexadecyl, octadecyl, docosyl radicals, also unsaturated and polyunsaturated species, such as, for example, oleyl, and $R^3$ is hydrogen or methyl. Other preferred amines are aminoalcohols, for example ethanolamine, amino-functionalized polyethylene glycols, diethanolamine, aminopropanol, their N-methyl derivatives, and their addition products of 1–30 mol of ethylene oxide and/or propylene oxide, also containing alkoxy-terminated, particularly preferably methoxy-terminated, polyoxyalkylene chains, and their acylation products, for example with straight-chain or branched, saturated or unsaturated carboxylic acids having from 1 to 30 carbon atoms, particularly preferably having from 8 to 24 carbon atoms.

The reaction can be carried out with or without the addition of organic solvents. Examples of suitable solvents are alcohols, ketones, esters, oligo- and poly(alkylene) glycols and glycol ethers, dimethyl sulfoxide, dimethylformamide, N,N-dimethylacetamide or N-methylpyrrolidone and their mixtures, etc. Preference is given to using alcohols having 2 to 4 carbon atoms, particularly preferably the short-chain alcohol $R^6OH$, and ketones such as, for example, methyl isobutyl ketone or methyl isoamyl ketone, or alkyl esters of carboxylic acids having 1 to 4 carbon atoms, such as, for example, sec-butyl acetate or pentyl acetate.

The reaction can optionally be carried out in the presence of compatibility-promoting agents. These may be surface-active compounds, for example addition products of from 1 to 30 mol of ethylene oxide and/or from 0 to 5 mol of propylene oxide with $C_{12}$–$C_{30}$-fatty alcohols and wool wax alcohols; ethylene oxide addition products of glycerol mono- and diesters and sorbitan mono- and diesters of saturated and unsaturated fatty acids having from 6 to 22 carbon atoms; addition products of from 2 to 30 mol of ethylene oxide and/or from 0 to 5 mol of propylene oxide with fatty acids having from 12 to 22 carbon atoms and with alkylphenols having from 8 to 15 atoms in the alkyl group, $C_{12}$–$C_{18}$-fatty acid partial esters of addition products of from 1 to 30 mol of ethylene oxide with glycerol; addition products of ethylene oxide with fats and oils, for example castor oil or hydrogenated castor oil; partial esters of saturated or unsaturated $C_{12}$–$C_{22}$-fatty acids, including branched or hydroxyl-substituted ones, with polyols, for example esters of glycerol, ethylene glycol, polyalkylene glycols, pentaerythritol, polyglycerol, sugar alcohols, such as sorbitol, and polyglucosides, such as cellulose; polysiloxane-polyalkyl-polyether copolymers and their derivatives and hydrophobically modified polyaspartic acid derivatives, for example partially esterified polyaspartic acids, partially esterified polyaspartic acid-co-glutamic acid or condensates of maleic monoesters and ammonia, prepared, for example, by the novel process or as in DE 195 45 678 A, the preparation process of said polyamino acid derivatives having no influence on their compatibility-promoting effect. If desired, a certain fraction of the product mixture may also remain in the reactor and be used as solubilizer for a subsequent reaction.

The compatibility- or solubility-promoting agents present may also be cationic surfactants, for example from the group of quaternary ammonium compounds, quaternized protein hydrolysates, alkylamido amines, quaternary ester compounds, quaternary silicone oils, quaternary sugar and polysaccharide derivatives, anionic surfactants, for example from the group of sulfates, sulfonates, carboxylates and mixtures thereof, for example alkylbenzenesulfonates, α-olefinsulfonates, α-sulfonated fatty acid esters, fatty acid glycerol ester sulfates, paraffinsulfonates, alkyl sulfates, alkyl polyether sulfates, alkyl sulfosuccinates, fatty acid salts (soaps), fatty acid esters of polylactic acid, N-acylamino acid esters, N-acyltaurates, acylisethionates, ether carboxylates, monoalkyl phosphates, N-acylamino acid derivatives, such as N-acylaspartates or N-acylglutamates, N-acylsarcosinates, amphoteric or zwitterionic surfactants, such as, for example, alkylbetaines, alkylamidoalkylbetaines of the cocoamidopropylbetaine type, sulfobetaines, phosphobetaines, sultaines and amidosultaines, imidazolinium derivatives, amphoglycinates, or nonionic surfactants, such as, for example, ethoxylated fatty alcohols, ethoxylated alkylphenols, ethoxylated fatty acid esters, ethoxylated mono-, di- or triglycerides or polyalkylene glycol fatty acid esters, sugar esters, for example fatty acid esters of sucrose, fructose or of methyl glucoside, sorbitol fatty acid esters and sorbitan fatty acid esters (optionally ethoxylated), alkyl or alkenyl polyglucosides and their ethoxylates, fatty acid N-alkylpolyhydroxyalkylamides, polyglycerol esters, fatty acid alkanolamides, long-chain tertiary amine oxides or phosphine oxides and dialkyl sulfoxides.

The compatibility-promoting agents preferably remain in the product. The reaction to give the copolymer is carried out in a preferred procedure with aqueous or gaseous ammonia at temperatures of from 0 to 150° C., preferably 50–140° C., and subsequent distillation is carried out at from 70 to 240° C., preferably from 110 to 150° C., under reduced pressure, for example in kneading devices, high-viscosity reactors, extruders or stirred reactors, optionally using high-shear force stirrers such as Mig or Intermig stirrers.

Under the reaction conditions, some of the ester groups, preferably those derived from $R^6OH$, are also hydrolyzed and, in addition to the polyether groups, other hydrophilic groups in the form of carboxylic acid or carboxylate groups are liberated. Subsequent mild partial or complete hydrolysis of other ester functions can, if desired, increase further the amount of free acid groups, for example by reaction with water, optionally in the presence of acids or bases, or with alkali metal hydroxides, optionally in the presence of an organic solvent or cosolvent.

The ester and amide components can also be mixtures of compounds having different radicals $R^2$, $R^3$, $R^4$, $R^5$ and $R^6$.

Another option is to react maleic anhydride with the corresponding alcohols and amines and carry out condensation in situ without isolation of the maleic monoesters and -amides by the novel process.

Without limiting the invention thereto, the structure for the novel condensation products is a polymeric structure essentially derived from polyaspartic acid and containing structural units of the general formulae (I) and/or (II), the structural elements A being identical or different trifunctional hydrocarbon radicals having 2 carbon atoms of the structure (A1) or (A2),

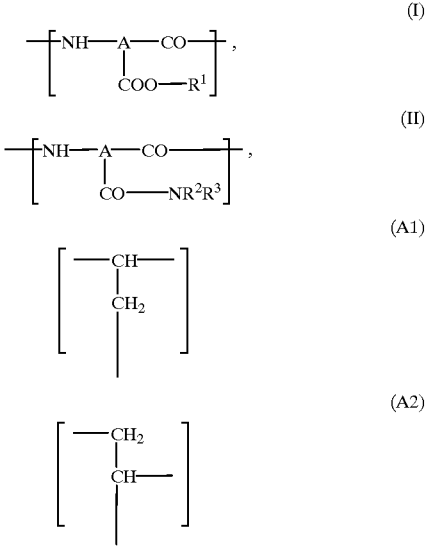

Instead of the maleic acid derivatives described, or in any mixture therewith, it is also possible to use analogous derivatives of fumaric acid. Furthermore, as well as maleic or fumaric acid derivatives, novel condensation products can also be prepared from the analogous derivatives of itaconic acid, alkenylsuccinic acid, alkylmaleic acid, citraconic acid, which are present in the reaction mixtures in amounts from 0 to 100%, preferably from 0 to 20%.

The addition of amino- and carboxy-functional compounds to the reaction mixture can give novel condensation products in which the added compounds are present bonded via amide bonds. Suitable units are amino acids from the group of the 20 proteinogenic acids which are present as monomers in all natural proteins, in enantiomerically pure or racemic form, such as, for example, glutamic acid, glutamine, asparagine, lysine, alanine, glycine, tyrosine, tryptophan, serine and cysteine and their derivatives, or nonproteinogenic amino acids having in each case one or more amino or carboxyl functions, such as, for example, β-alanine, ω-amino-1-alkanoic acids. The units are added, in an amount of from 0 to 20% by weight, to the starting mixture of the maleic acid derivatives or, to modify the chain ends, are reacted therewith after the polymers have been synthesized in the usual manner, preferably with the addition of polar solvents, such as, for example, alcohols or dimethylformamide.

By adding cocondensable compounds to the reaction mixture, such as mono-, di- or polycarboxylic acids such as, for example, maleic acid, fumaric acid, itaconic acid or saturated or unsaturated $C_8$–to $C_{22}$-alkycarboxylic acids, and also hydroxy-functional carboxylic acids such as, for example, tartaric acid, citric acid, malic acid, and the derivatives of said cocondensable acids, for example their esters, amides or anhydrides, it is possible to further modify the condensation product. These additives can be present in from 0 to 20% by weight, based on the starting mixture.

The molecular masses of the condensation products can be increased by adding di- and/or polyfunctional units, derived from a di- or polyhydroxy compound, of a di- or polyamino compound or amino alcohols, having a linear, branched or cyclic, saturated, unsaturated or aromatic hydrocarbon backbone, optionally oxo or aza analogs with O or N atoms in the chain, or from polyalkylene glycols or ethylene oxide-propylene oxide copolymers. The molecular-weightincreasing groups are inserted by adding polyfunctional amino or hydroxyl compounds or their reaction products with maleic anhydride to the reaction mixture or to the polymers formed, optionally with the addition of acidic or Lewis acid catalysts.

The resulting polymers can be post-treated, for example by treatment with ammonia, transesterification catalysts such as, for example, Lewis acid titanium(IV) compounds, with activated charcoal or other adsorbents, by bleaching with oxidizing agents such as $H_2O_2$, $Cl_2$, $O_3$, sodium chlorite, sodium hypochlorite etc. or reducing agents such as, for example, $NaBH_4$ or $H_2$ in the presence of catalysts, or the addition of ethylene oxide and/or propylene oxide.

Typical representatives of the novel condensation products in the nonneutralized form have, for example, the following composition. The formula shows the idealized linking in the (-position, it being possible for at least some (-linking also to be present in the products:

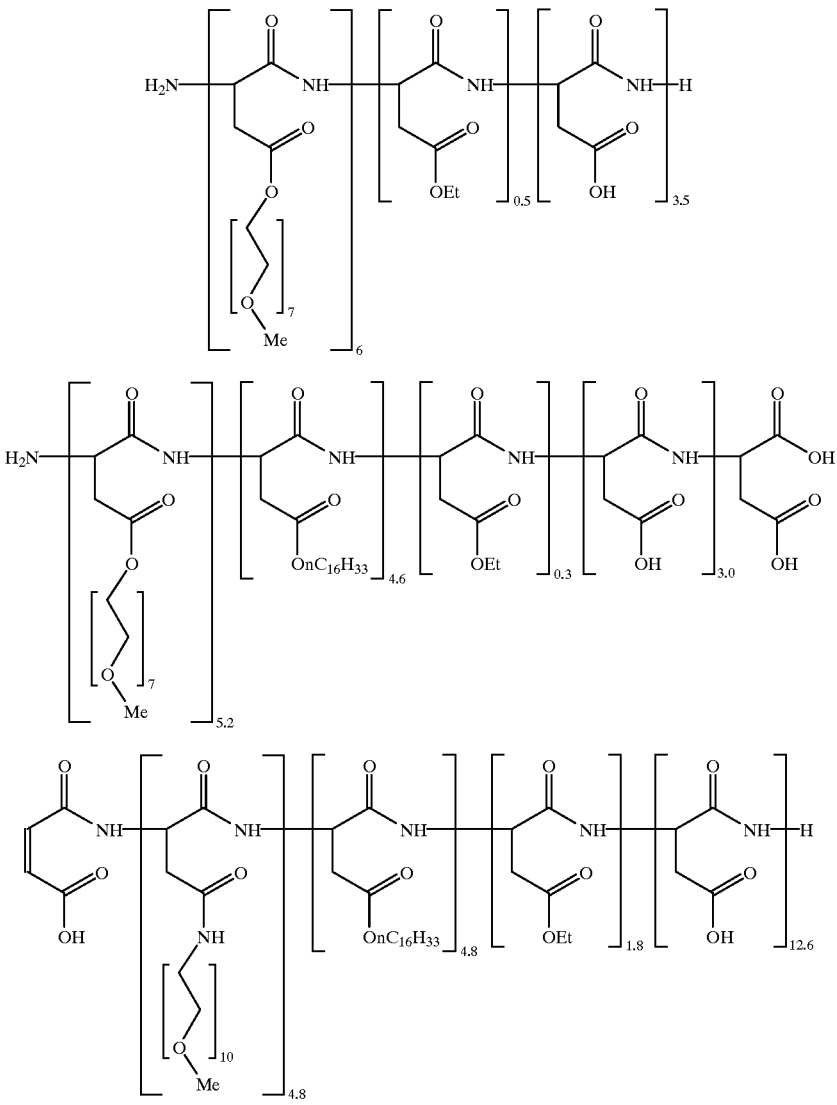

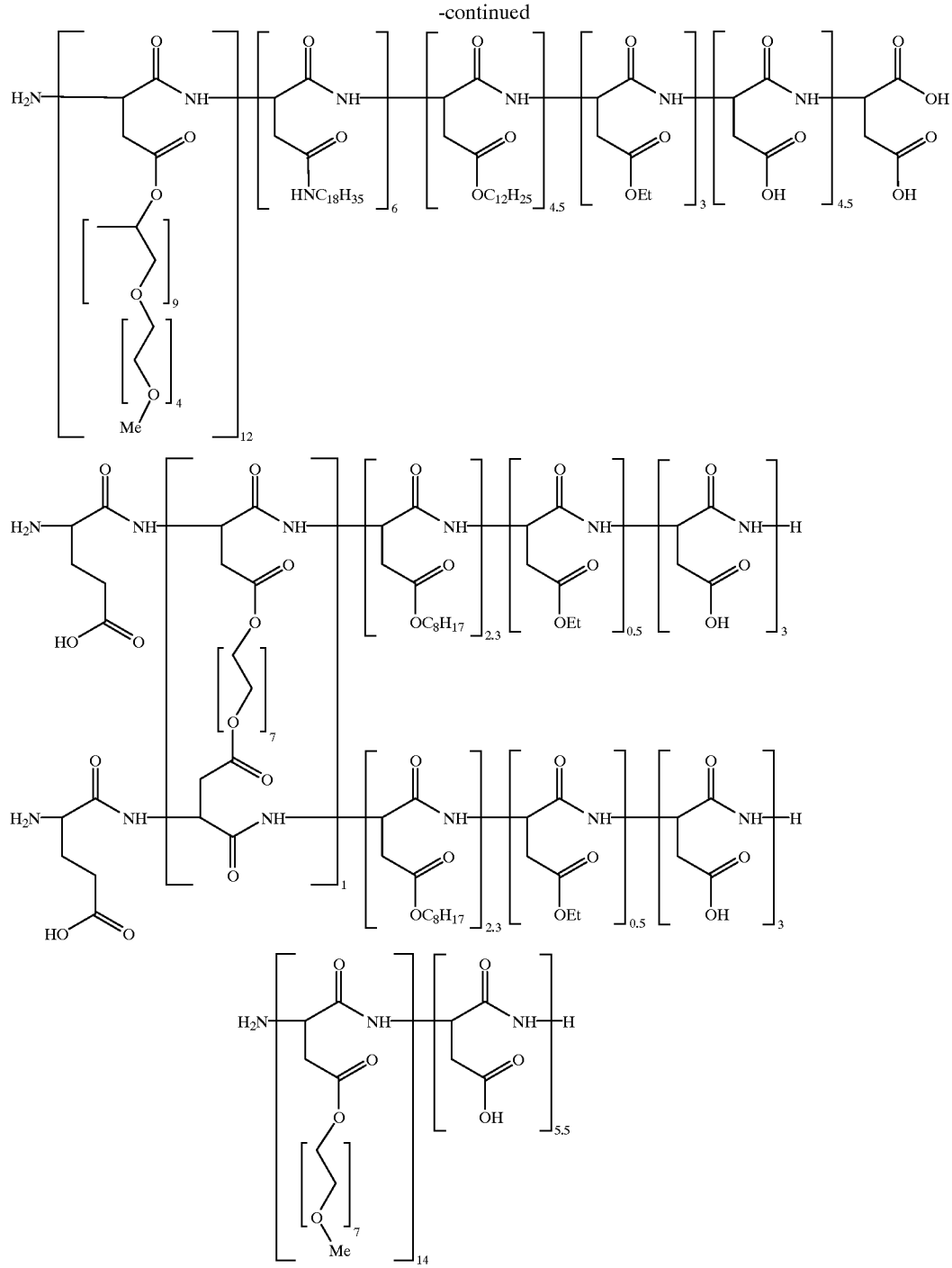

The novel copolymers have excellent properties as sequestering agents, as additives for colorants and coatings, as foam stabilizers, surfactants and emulsifiers. In particular, the pH, thermal and long-term stability of O/W and W/O emulsions is beneficial influenced.

The novel polymers can be used as O/W emulsifiers for cosmetic emulsions, for example for lotions having a comparatively low viscosity or creams and ointments having a high viscosity, for applications as skin care compositions, such as, for example, day creams, night creams, care creams, nourishing creams, body lotions, ointments and the like. Other auxiliaries and additives which may be present are customary coemulsifiers, bodying agents, oily substances, superfatting agents, fats, waxes, stabilizers, active ingredients, glycerol, dyes and fragrances.

Suitable bodying agents which may be used are hydrophilic waxes, for example $C_{12}$–$C_{30}$ fatty alcohols, $C_{16}$–$C_{22}$ fatty acids, glycerol mono- and diesters and sorbitan mono- and diesters of saturated fatty acids having from 12 to 22 carbon atoms.

Examples of other suitable coemulsifiers are: addition products of from 2 to 30 mol of ethylene oxide and/or from 0 to 5 mol of propylene oxide with $C_{12}$–$C_{30}$ fatty alcohols and wool wax alcohols, preferably linear, saturated $C_{16}$–$C_{22}$ fatty alcohols; ethylene oxide addition products of glycerol mono- and diesters and sorbitan mono- and diesters of saturated and unsaturated fatty acids having from 6 to 22 carbon atoms; addition products of from 2 to 30 mol of ethylene oxide and/or from 0 to 5 mol of propylene oxide with fatty acids having from 12 to 22 carbon atoms and with alkylphenols having from 8 to 15 carbon atoms in the alkyl group; $C_{12}$–$C_{18}$ fatty acid partial esters of addition products of from 1 to 30 mol of ethylene oxide with glycerol; addition products of ethylene oxide with fats and oils, for example castor oil or hydrogenated castor oil; partial esters of saturated or unsaturated $C_{12}$–$C_{22}$ fatty acids, including branched or hydroxy-substituted ones, with polyols, for example esters of glycerol, ethylene glycol, polyalkylene glycols, pentaerythritol, polyglycerol, sugar alcohols such as sorbitol and polyglucosides such as cellulose; polysiloxane-polyalkyl-polyether copolymers and their derivatives and hydrophobically modified polyaspartic acid derivatives.

The selected coemulsifiers may also be anionic, cationic, nonionic, amphoteric and/or zwitterionic surfactants, for example from the group referred to as compatibility-promoting agents.

It is possible in each case to use any mixtures of the above bodying agents and coemulsifiers.

Examples of suitable oily substances are esters of linear $C_6$–$C_{20}$ fatty acids with linear $C_6$–$C_{20}$ fatty alcohols, esters of branched $C_6$–$C_{13}$ carboxylic acids with linear $C_6$–$C_{20}$ fatty alcohols, esters of linear $C_6$–$C_{20}$ fatty acids with branched alcohols, esters of linear and/or branched $C_6$–$C_{20}$ carboxylic acids with polyhydric alcohols and/or Guerbet alcohols, triglycerides based on $C_6$–$C_{10}$ fatty acids, vegetable and animal oils and fats, branched primary alcohols, substituted cyclohexanes, Guerbet carbonates, dialkyl ethers and/or aliphatic or naphthenic hydrocarbons.

Suitable superfatting agents are, for example, lanolin and lecithin derivatives and their ethoxylates, polyol fatty esters, monoglycerides and fatty acid alkanolamides. Silicone compounds such as polydimethylsiloxanes, cyclodimethicones and amino-, fatty-acid-, alcohol-, epoxy-, fluorine-, and/or alkyl-modified silicone compounds, and waxes such as, for example, beeswax, paraffin waxes or microcrystalline waxes may be present. The emulsions may comprise thickeners, such as polyacrylic acid derivatives or cationic polymers such as, for example, cationic cellulose or starch derivatives, cationic chitin or chitosan derivatives, cationic silicone polymers, copolymers of diallylammonium salts e.g. with acrylamides, polyethylenimine. Furthermore, metal salts of fatty acids, e.g. magnesium, aluminum or zinc stearate, may be present as stabilizers, or zinc salts of ricinoleic acid may be present as deodorizers. Customary sunscreen active ingredients such as titanium dioxide, p-aminobenzoic acid etc., fragrances, dyes, biogenic active ingredients such as plant extracts or vitamin complexes and pharmaceutical active ingredients may be present. The emulsions may further comprise lusterizing agents, such as ethylene glycol distearate and customary preservatives such as parabens, sorbic acid, phenoxyethanol and others.

The novel polyaspartic acid derivatives can also be used in W/O emulsions, for example as emulsifiers and/or coemulsifiers for the preparation of skincare creams and lotions.

The novel polyaspartic acid derivatives having a polyamino acid backbone which is similar to naturally occurring structures are mild surfactants which can be used alone or in combination with anionic, cationic, nonionic, zwitterionic and/or amphoteric surfactants. Solid, liquid or paste preparations are possible, e.g. soap bars, washing lotions, shower gels, shampoos.

The surfactants which can be used in combination with the novel polyaspartic acid derivatives can for example be anionic surfactants from the group of sulfates, sulfonates, carboxylates and mixtures thereof. The anionic groups can be in neutralized form, containing cationic counterions from the group of alkali metals, alkaline earth metals, ammonium or substituted ammonium. Use can be made, for example, of alkylbenzenesulfonates, α-olefinsulfonates, α-sulfonated fatty esters, fatty acid glycerol ester sulfates, paraffinsulfonates, alkyl sulfates, alkyl polyether sulfates, alkyl sulfosuccinates, fatty acid salts (soaps), fatty acid esters of polylactic acid, N-acylamino acid esters, N-acyltaurates, acylisethionates, ether carboxylates, monoalkyl phosphates, N-acylamino acid derivatives, such as N-acylaspartates or N-acylglutamates, N-acylsarcosinates, polyaspartic acid derivatives and others.

The surfactants which can be used in combination with the novel polyaspartic acid derivatives can, for example, be amphoteric or zwitterionic surfactants, for example alkylbetaines, alkylamidoalkylbetaines of the cocoamidopropylbetaine type, sulfobetaines, phosphobetaines, sultaines and amidosultaines, imidazolinium derivates, amphoglycinates and others.

The cationic surfactants which can be used in combination with the novel polyaspartic acid derivatives can, for example, be from the group of quaternary ammonium compounds, quaternized protein hydrolysates, alkylamido amines, quaternary ester compounds, quaternary silicone oils or quaternary sugar and polysaccharide derivatives.

The surfactants which can be used in combination with the novel polyaspartic acid derivatives can, for example, be nonionic surfactants, for example ethoxylated fatty alcohols, ethoxylated alkylphenols, ethoxylated fatty acid esters, ethoxylated mono-, di- or triglycerides or polyalkylene glycol fatty acid esters. Other nonionic surfactants can originate from the group of alkyl polysaccharides, for example alkyl or alkenyl polyglucosides, sugar esters, for example fatty acid esters of glucose, sucrose, fructose or of methyl glucoside, sorbitol fatty acid esters and sorbitan fatty acid esters (optionally ethoxylated), polyglycerol esters, fatty acid alkanolamides, N-acylamino sugar derivatives, for example N-acylglucamines, long-chain tertiary amine oxides or phosphine oxides and dialkyl sulfoxides.

The surfactants which can be used in combination with the novel polyaspartic acid derivatives can thus also be any combinations of two or more surfactants from the above categories.

The surfactant preparations according to the invention can comprise further auxiliaries and additives, such as, for example, water and solvents, for example from the group of alcohols and polyols, thickeners, opacifiers, e.g. glycol ester derivatives; moisturizers, emollients such as animal and vegetable oils, carboxylic esters, lanolin, beeswax, silicones; polymeric agents for improving the feel on the skin, conditioning, care or pharmaceutically active constituents such as, for example, cationic or amphoteric polymers, proteins and protein derivatives, lanolin derivatives, pantothenic acid, betaine, polydimethylsiloxanes or their derivatives, sunscreen active ingredients and solubilizers, stabilizers, fragrances, buffer substances, preservatives and/or dyes.

The surfactant preparations comprising polyaspartic acid derivatives can advantageously be used in, for example, hair shampoos, shower preparations, bubble bath preparations, hand, face and intimate area cleansing lotions, liquid soaps, soap bars, shaving creams, handwashing pastes, dishwashing detergents which are gentle on the skin, cleaners for smooth surfaces and in toothpastes.

The novel polyaspartic acid derivatives can be used as dispersants, for example for coatings and colorants. They effect a favorable color strength development and an improvement in the rub-out properties.

The novel hydrophobically modified polyaspartic acid derivatives are, if they are not already present as a salt, neutralized advantageously using prior art neutralizing agents, in particular amines. Particular preference is here given to using dimethylethanolamine or 2-amino-2-methylpropanol. For the preparation of aqueous pigment pastes, 0.1 to 100% by weight, preferably 0.5 to 50% by weight, in particular 2 to 15% by weight, based on the weight of the pigments, are used. The hydrophobically modified polyaspartic acid derivatives can, for the novel use, either be mixed beforehand with the pigments to be dispersed, or be dissolved directly in the dispersing medium (water, possible additions of glycol) prior to or at the same time as the addition of the pigments and any other solids. Neutralization can take place before or during preparation of the pigment pastes. Preference is given to using polyaspartic acid preparations which have already been partially or completely neutralized.

The novel polyaspartic acid derivatives can also be used in any mixtures with other, prior art dispersion additives, for example from the group of fatty acid alkoxylates, poly (meth)acrylates, polyesters, polyethers etc.

In this connection, examples of pigments which may be mentioned are inorganic or organic pigments, and carbon blacks. Fillers which can, for example, be dispersed in aqueous coatings are, for example, those based on kaolin, talc, other silicates, chalk, glassfibers, glass beads or metal powders. Examples of inorganic pigments are titanium dioxide and iron oxides. Suitable organic pigments are, for example, azo pigments, metal complex pigments, phthalocyanine pigments, anthraquinoid pigments, polycyclic pigments, in particular those from the thioindigo, quinacridone, dioxazine, pyrrolopyrrole, naphthalenetetracarboxylic acid, perylene, isoamidolin(on)e, flavanthrone, pyranthrone or isoviolanthrone series.

Suitable coating systems into which the novel pigment pastes can be incorporated are any aqueous 1-component or 2-component coatings. Examples include aqueous 1-component coatings, such as, for example, those based on alkyd, acrylate, epoxy, polyvinyl acetate, polyester or polyurethane resins, or aqueous 2-component coatings, for example those based on hydroxyl-group-containing polyacrylate or polyester resins with melamine resins or optionally blocked polyisocyanate resins as crosslinkers. Polyepoxy resin systems may likewise also be mentioned.

The novel polyaspartic acid derivatives can be used as complexing agents, for example in detergents, as encrustation inhibitors, as metal deactivators in plastics, as auxiliaries in the leather and textile industries or as activity-enhancing additives for pesticides or insecticides. High molecular weight derivatives, preferably after modification with the abovementioned polyfunctional hydroxy and amino compounds, are also suitable as absorber materials.

EXAMPLES

The novel condensation of modified monoesters and/or -amides of α,β-unsaturated dicarboxylic acids was carried out by reacting the starting materials (maleic monoester, N-substituted maleic acid monoamide) in methyl isobutyl ketone with from 1.0 to 1.5 equivalents of ammonia gas and heating under reduced pressure at 120–140° C. for from 4 to 6 h. The degree of esterification of the polyaspartic acid side chains was determined using NMR spectroscopy, and the data are in mol %.

Example 1

The reaction of 1.1 mol of cetyl maleate and 3.0 mol of the addition product of equimolar amounts of maleic anhydride and polyethylene glycol-7 monomethyl ether with 5.4 mol of ammonia in methyl isobutyl ketone and thermal treatment for 4.5 h at 120° C. and pressure reduction to 20 mbar with distillation gave a condensation product containing 23% cetyl ester and 62% polyoxyethylene ester.

Example 2

The reaction of 0.5 mol of N-stearylmaleamide, 2.0 mol of ethyl maleate and 1.5 mol of the addition product of equimolar amounts of maleic anhydride and polyethylene glycol-7 monomethyl ether with 5.5 mol of ammonia in methyl isobutyl ketone and thermal treatment for 5 h at from 120 to 130° C. and pressure reduction to 20 mbar with distillation gave a condensation product containing 11% N-stearylamide and 31% polyoxyethylene ester, 8% ethyl ester and 50% acid groups.

Example 3

The reaction of 1.5 mol of decyl maleate, 1.0 mol of ethyl maleate and 1.5 mol of the addition product of equimolar amounts of maleic anhydride and polyethylene glycol-12 monomethyl ether with 5.5 mol of ammonia in n-decanol and thermal treatment for 5 h at 120° C. and pressure reduction to 20 mbar with distillation gave a condensation product containing 29% decyl ester, 32% polyoxyethylene ester, 4% ethyl ester and 35% acid groups.

Comparative Example 1

The condensation of 1.2 mol of cetyl maleate and 2.8 mol of ethyl maleate with 5.2 mol of ammonia in methyl isobutyl ketone gave a product containing 27% cetyl ester and 6% ethyl ester.

Examples 4–7

O/W emulsions containing polyaspartic acid derivatives

| | |
|---|---|
| Polyaspartate derivative (25% in water, adjusted to pH 5.5 using NaOH) | 2.0% |
| Glycerol | 3.0% |
| Preservative | 0.1% |
| Water | 70.4% |
| Glycerol monostearate (Tegin M, Th. Goldschmidt) | 4.5% |
| Tegosoft ® ( CT (caprylic/capric triglyceride, Th. Goldschmidt) | 20.0% |

The aqueous phase, adjusted to the pH given in the table using sodium hydroxide solution, and the oily substance/glycerol monostearate mixture are mixed at 70° C. and processed vigorously using a rotor-stator homogenizer (SG/220V, 2 min). The emulsion (100 ml) is stored for 2 days at 20° C. and 28 d at 45° C. The water separation in the O/W emulsions was determined after storage for 2 days at 20° C. and after storage for a further 28 d at 45° C.

| Example | Emulsifier from Example | pH of the aqueous phase | Water separation after 2 d, 20° C. (% by volume) | Water separation after 28 d, 45° C. (% by volume) |
|---|---|---|---|---|
| 3 | 1 | 5.5 | <0.1 | 5 |
| 4 | 1 | 7.0 | <0.1 | 5 |
| 5 (Comparison) | Comp. Ex. 1 | 5.5 | <0.1 | 6 |
| 6 (Comparison) | Comp. Ex. 1 | 7.0 | 0.4 | 15 |

These results show the improved emulsion stability in variable pH ranges when using the products obtained by condensation of monoesters and optionally -amides, which have been modified in accordance with the invention, of α,β-unsaturated dicarboxylic acids.

While the invention has been particularly shown and described with respect to preferred embodiments thereof, it will be understood by those skilled in the art that the foregoing and other changes in form and details may be made therein without departing from the spirit and scope of the invention.

What is claimed is:

1. A cosmetic W/O or O/W emulsion comprising at least one condensation product containing polyoxyalkylene chains bonded by ester and by amide bonds, prepared from either monoesters and monoamides of monoethylenically unsaturated dicarboxylic acids and ammonia or from the ammonium salt of said acids, and the mixture thereof, wherein said condensation product has a total content from 1 to less than 100%, by weight, of said monoesters and from greater than 0 to 99%, by weight, of said monoamides.

2. The cosmetic W/O or O/W emulsion as claimed in claim 1 wherein said condensation product contains identical or different, straight-chain or branched, saturated or unsaturated alkyl or alkenyl radicals having from 1 to 30 carbon atoms and bonded via ester and amide bonds.

3. The cosmetic W/O or O/W emulsion as claimed in claim 1 wherein said condensation product contains identical or different, straight-chain or branched, saturated or unsaturated alkyl or alkenyl radicals having from 6 to 30 carbon atoms and bonded via ester and amide bonds.

4. The cosmetic W/O or O/W emulsion as claimed in claim 1 wherein said condensation product is prepared from maleic acid derivatives of the general formulae (I) and (II)

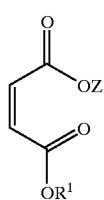

(I)

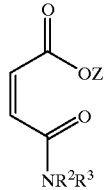

(II)

where
$R^1$ is $R^4$, R or $R^6$;
$R^2$ is identical or different, straight-chain or branched, saturated or unsaturated alkyl, alkenyl or aryl radicals having from 1 to 30 carbon atoms, hydroxy- or aminoalkyl, each optionally oxa- or aza-substituted, having from 1 to 6 hydroxyl groups, from 1 to 6 amino groups or both, acylation products with $C_1$ to $C_{22}$ carboxylic acid radicals, or polyoxyalkylene radicals having the formula $R^{12}X(C_nH_{2n-m}R^{13}{}_mO)_oR^{14}$, where X is oxygen or the radical —NH—, $R^{12}$ is identical or different divalent alkyl, alkenyl or aryl radicals having from 2 to 30 carbon atoms, $R^{13}$ is hydrogen, identical or different alkyl, alkenyl or aryl radicals having from 1 to 30 carbon atoms, or a combination thereof, $R^{14}$ is hydrogen, or identical or different alkyl, alkenyl, aryl or acyl radicals having from 1 to 30 carbon atoms, n is 2 or 4, m is from 0 to 4 and o is from 1 to 100, or is the meaning of $R^5$;
$R^3$ is hydrogen or a radical $R^2$;
$R^4$ is identical or different, straight-chain or branched, saturated or unsaturated hydroxy-functional alkyl or alkenyl radicals having from 1 to 30 carbon atoms and from 1 to 20 hydroxyl groups, acylation products with $C_1$ to $C_{22}$ carboxylic acid radicals, or polyoxyalkylene radicals having the formula $R^{12}X(C_nH_{2n-m}R^{13}{}_mO)_oR^{14}$, where X is oxygen, or the radical —NH—, $R^{12}$ is identical or different divalent alkyl, alkenyl or aryl radicals having from 2 to 30 carbon atoms, $R^{13}$ is hydrogen, identical or different alkyl, alkenyl or aryl radicals having from 1 to 30 carbon atoms, or combination thereof, $R^{14}$ is hydrogen, identical or different alkyl or aryl radicals having from 1 to 30 carbon atoms, n is 2 or 4, m is from 0 to 4 and o is from 1 to 100;
$R^5$ is identical or different, straight-chain or branched, saturated or unsaturated alkyl or alkenyl radicals $R^7$ having from 6 to 30 carbon atoms, or radicals of the structure —Y—$R^7$, where Y is a polyoxyalkylene radical having the formula $(C_nH_{2n-m}R^{13}{}_mO)_o$, where $R^{13}$ is hydrogen, identical or different alkyl, alkenyl or aryl radicals having from 1 to 30 carbon atoms, or a combination thereof, n is 2 or 4, m is from 0 to 4, and o is from 1 to 100, and $R^6$ is identical or different, straight-chain or branched, saturated or unsaturated alkyl or alkenyl radicals having from 1 to 5 carbon atoms;
Z is one or more radicals from the group of alkali metals, alkaline earth metals, hydrogen or ammonium, $(NR^8R^9R^{10}R^{11})^+$, where $R^8$ to $R^{11}$ are independently hydrogen, identical or different, straight-chain or branched, saturated or unsaturated alkyl radicals or hydroxy-functional alkyl radicals having from 1 to 22 carbon atoms and optionally from 1 to 6 hydroxyl groups;
and at least one radical $R^2$, $R^3$ or $R^4$ contains a polyoxyalkylene chain having from 2 to 100 units, with the proviso that $R^4$ is not said radicals Y bonded to a radical $R^7$.

5. The cosmetic W/O or O/W emulsion as claimed in claim 1 wherein said condensation product is obtainable by reaction of the monoesters and monoamides of flumaric acid, itaconic acid, alkenylsuccinic acid, alkylmaleic acid, citraconic acid, or a combination thereof, wherein said citraconic acid is employed alone or as a mixture with the maleic acid derivatives.

6. The cosmetic W/O or O/W emulsion as claimed in claim 1, wherein said condensation product is obtainable by reaction of maleic monoesters of hydroxy-functional polyoxyalkylenes and maleic monoesters of alcohols having the formula $R^5OH$, $R^6OH$, or a combination thereof, or amides of maleic acid derived from amines having the formula $NR^2R^3H$, where $R^2$, $R^3$, $R^5$ and $R^6$ are as defined above, said amides of maleic acid being used alone or in combination with one of said alcohols.

7. The cosmetic W/O or O/W emulsion as claimed in claim 3, wherein said condensation product is obtainable by reaction of maleic monoamide of amino-functional polyoxyalkylenes and maleic monoesters of alcohols having the formula $R^5OH$, $R^6OH$, or a combination thereof, or amides of maleic acid derived from amines having the formula $NR^2R^3H$, where $R^2$, $R^3$, $R^5$ and $R^6$ are as defined above, said amides of maleic acid being used alone or in combination with one of said alcohols.

8. The cosmetic W/O or O/W emulsion as claimed in claim 1 wherein said condensation product is prepared in the presence of up to 20% by weight of cocondensable compounds, said cocondensable compounds are selected from the group consisting of proteinogenic or nonproteinogenic amino acids, mono-, di- or polyfunctional carboxylic acids, and their esters, amides, anhydrides or their salts.

9. The cosmetic W/O or O/W emulsion as claimed in claim 1 wherein said condensation product is prepared in the presence of agents which increase molecular mass, said agents are selected from the group consisting of di- or polyhydroxy compounds, di- or polyamino compounds, aminoalcohols or mixtures thereof, having a linear, branched or cyclic, saturated or aromatic hydrocarbon backbone, optionally oxo-or aza-substituted with O or N atoms in the chain, and their reaction products with maelic anhydride.

10. The cosmetic emulsion as claimed in claim 1, wherein said emulsion comprises a nonaqueous fraction comprises from 5 to 99% by weight of oily substances selected from the group consisting of esters of linear $C_6$–$C_{20}$-fatty acids with linear $C_6$–$C_{20}$-fatty alcohols; esters of branched $C_6$–$C_{13}$-carboxylic acids with linear $C_6$–$C_{20}$-fatty alcohols; esters of linear $C_6$–$C_{20}$-fatty acids with branched alcohols; esters of linear, branched, or a combination of linear and branched $C_6$–$C_{20}$-carboxylic acids with polyhydric alcohols, Guerbet alcohols, or a combination of said alcohols; triglycerides based on $C_6$–$C_{10}$-fatty acids; vegetable and animal oils and fats; branched primary alcohols; substituted cyclohexanes; Guerbet carbonates; dialkyl ethers; and aliphatic or naphthenic hydrocarbons.

11. The cosmetic O/W emulsion as claimed in claim 1, wherein hydrophilic waxes from the group consisting of $C_{12}$–$C_{30}$-fatty alcohols, wool wax alcohols, $C_{16}$–$C_{22}$-fatty acids, glycerol mono- and diesters and sorbitan mono- and diesters of saturated fatty acids having from 12 to 22 carbon atoms are present.

12. The cosmetic emulsion as claimed in claim 1, wherein one or more coemulsifiers selected from the group consisting of the addition products of ethylene oxide or ethylene oxide and propylene oxide with $C_{12}$–$C_{30}$-fatty alcohols and wool wax alcohols, of the ethylene oxide addition products of glycerol mono- and diesters and sorbitan mono- and diesters of saturated and unsaturated fatty acids having from 6 to 22 carbon atoms, of the addition products of ethylene oxide and/or propylene oxide with fatty acids having from 12 to 22 carbon atoms and with alkylphenols having from 8 to 15 carbon atoms in the alkyl group, of $C_{12}$–$C_{18}$-fatty acid mono- and diesters of addition products of ethylene oxide with glycerol, of addition products of ethylene oxide with fats and oils, of polyol esters of saturated or unsaturated $C12$–$C_{22}$-fatty acids, polysiloxane-polyalkyl-polyether copolymers and their derivatives, of anionic surfactants, cationic surfactants, nonionic surfactants and zwitterionic or amphoteric surfactants are present.

13. A surface active preparation for cleaners and/or cosmetic compositions comprising a condensation product containing polyoxyalkylene chains bonded by ester and by amide bonds, prepared from either monoesters and monoamides of monoethylenically unsaturated dicarboxylic acids and ammonia or from the ammonium salt of said acids, and the mixture thereof, wherein said condensation product has a total content from 1 to less than 100%, by weight, of said monoesters and from greater than 0 to 99%, by weight, of said monoamides, optionally comprising one or more further surfactants selected from the group consisting of anionic, cationic, nonionic, amphoteric, zwitterionic surfactants and mixtures thereof, customary auxiliaries and additives.

14. The cosmetic W/O or O/W emulsion as claimed in claim 1 wherein said polyoxyalkylene chains are present in a content of from 1 to 95% by weight.

15. The cosmetic W/O or O/W emulsion as claimed in claim 1 wherein said polyoxyalkylene chains are present in a content of from 20 to 80% by weight.

* * * * *